(12) United States Patent     (10) Patent No.:   US 12,670,990 B2

Jung           (45) Date of Patent:    Jun. 30, 2026

---

(54) SYSTEM FOR PROVIDING DIAGNOSTIC SCRIPT FOR SCALP AND HAIR LOSS CONDITION BASED ON ARTIFICIAL INTELLIGENCE ALGORITHM

(71) Applicant: ROOTONIX Co., Ltd., Seoul (KR)

(72) Inventor: Dae Kwon Jung, Seoul (KR)

(73) Assignee: ROOTONIX Co., Ltd., Seoul (KR)

( * ) Notice: Subject to any disclaimer, the term of this patent is extended or adjusted under 35 U.S.C. 154(b) by 352 days.

(21) Appl. No.: 18/214,534

(22) Filed: Jun. 27, 2023

(65) Prior Publication Data

US 2024/0221938 A1     Jul. 4, 2024

(30) Foreign Application Priority Data

Jan. 4, 2023    (KR) ........................ 10-2023-0001268
May 31, 2023    (KR) ........................ 10-2023-0070068

(51) Int. Cl.
    *G06K 9/00*      (2022.01)
    *G06T 7/00*      (2017.01)
    *G16H 50/20*     (2018.01)

(52) U.S. Cl.
    CPC ........... *G16H 50/20* (2018.01); *G06T 7/0012* (2013.01); *G06T 2207/20081* (2013.01); *G06T 2207/30088* (2013.01)

(58) Field of Classification Search
    None
    See application file for complete search history.

(56) References Cited

U.S. PATENT DOCUMENTS

2022/0375601 A1* 11/2022 Punyani ................ G06T 7/0012
2024/0049869 A1* 2/2024 Delapenha ............. A61B 5/448

FOREIGN PATENT DOCUMENTS

| KR | 10-2019-0123067 A | 10/2019 |
|----|-------------------|---------|
| KR | 10-2284579 B1 | 8/2021 |
| KR | 10-2022-0052532 B1 | 4/2022 |
| KR | 10-2398034 B1 | 5/2022 |
| KR | 10-2415710 B1 | 7/2022 |
| KR | 10-2022-0120807 A | 8/2022 |
| KR | 10-2499193 B1 | 2/2023 |

* cited by examiner

*Primary Examiner* — Wei Wen Yang
(74) *Attorney, Agent, or Firm* — Revolution IP, PLLC

(57) ABSTRACT

A system for providing diagnostic script for scalp and hair loss condition, includes a data receiving unit that receives scalp photographed image data of a patient to be diagnosed with a scalp condition and a hair loss condition; a classification unit that inputs the received scalp photographed image data of the patient into a first learning model that has been learned to acquire result values for a plurality of measurement items and classifies the scalp condition and the hair loss condition using the acquired result values; and a diagnosis result providing unit that inputs information on the classified scalp condition and hair loss condition into a second learning model and outputs diagnosis script data.

8 Claims, 6 Drawing Sheets

FIG. 5

| REFERENCE ITEMS FOR SCALP TYPE CLASSIFICATION | | | | | |
|---|---|---|---|---|---|
| Task | Classification | | | Object Detection | |
| CLASSIFICATION | KERATIN | OIL | SENSITIVITY | ERYTHEMA (INFECTION) | PUSTULES |
| DRY | ▨ | | | | |
| OILY | | ▨ | | | |
| SENSITIVE | | | ▨ | | |
| DANDRUFF | ▨ | | | | |
| ATOPIC | ▨ | | ▨ | | |
| SEBORRHEIC | | ▨ | | | |
| COMPLEX | | ▨ | | | |
| INFLAMMATORY | | | | ▨ | |
| PUSTULAR | | | | | ▨ |
| FOLLICULITIS | | | | ▨ | ▨ |

FIG. 6

| REFERENCE ITEMS FOR HAIR LOSS DIAGNOSIS | | | | |
|---|---|---|---|---|
| CLASSIFICATION | NUMBER OF HAIRS PER HAIR FOLLICLE | | HAIR THICKNESS | |
| | REFERENCE OR MORE | REFERENCE OR LESS | REFERENCE OR MORE | REFERENCE OR LESS |
| NORMAL | | | | |
| SUSPECTED HAIR LOSS | | | | |
| PROGRESSING HAIR LOSS | | | | |

SYSTEM FOR PROVIDING DIAGNOSTIC SCRIPT FOR SCALP AND HAIR LOSS CONDITION BASED ON ARTIFICIAL INTELLIGENCE ALGORITHM

This application is based on and claims priority under 35 U.S.C. § 119 to Korean Patent Application No. 10-2023-0001268, filed on Jan. 4, 2023, and Korean Patent Application No. 10-2023-0070068, filed on May 31, 2023 in the Korean Intellectual Property Office, the disclosure of which is incorporated by reference herein in its entirety.

TECHNICAL FIELD

One or more embodiments relate to a system for providing diagnostic script for scalp and hair loss condition based on artificial intelligence algorithm, and more particularly, to a system for providing diagnostic script that predicts scalp and hair loss condition using a learning model that has been learned using scalp photographed image data and expert diagnosis script data, and outputs a diagnosis script corresponding thereto.

BACKGROUND ART

The global anti-aging product market is expected to grow at an average annual rate of 5.2% between 2019 and 2025, reaching $51.5 billion in 2025, and particularly, interest in hair care and scalp care is increasing.

In addition, the potential hair loss population in Korea is also increasing, and accordingly, the hair loss care market is estimated to be about 4 trillion won.

Meanwhile, since non-face-to-face treatment was temporarily allowed to strengthen COVID-19 quarantine, the market for non-face-to-face treatment related to hair loss is also increasing.

However, the conventional non-face-to-face diagnosis technology has a limitation in that professionalism is poor because it stops at diagnosing the scalp condition using only the scalp photographed image data of the patient.

SUMMARY

As described above, according to the present disclosure, an object thereof is to provide a system for providing diagnostic script for scalp and hair loss condition based on artificial intelligence algorithm that predicts scalp and hair loss condition using a learning model that has been learned using scalp photographed image data and expert diagnosis script data, and outputs a diagnosis script corresponding thereto.

According to an embodiment of the present disclosure for achieving this technical problem, there is provided a system for providing diagnostic script for scalp and hair loss condition, including a data receiving unit that receives scalp photographed image data of a patient to be diagnosed with a scalp condition and a hair loss condition; a classification unit that inputs the received scalp photographed image data of the patient into a first learning model that has been learned to acquire result values for a plurality of measurement items and classifies the scalp condition and the hair loss condition using the acquired result values; and a diagnosis result providing unit that inputs information on the classified scalp condition and hair loss condition into a second learning model and outputs diagnosis script data.

The system for providing diagnostic script for scalp and hair loss condition may further include a data collection unit that collects scalp photographed image data and expert diagnosis script data; a labeling data collection unit that collects labeling data including scores and keywords for each measurement item corresponding to the scalp photographed image data and the expert diagnosis script data; and a learning unit that builds the first learning model and the second learning model, causes the built first learning model to learn to output the result values of the plurality of measurement items, and causes the second learning model to learn to generate a diagnostic script using a classification result output through the first learning model.

The measurement items may include at least one of keratin, oil, sensitivity, hair thickness, the number of hairs per hair follicle, erythema, and pustules.

The learning unit may cause the first learning model to learn to extract result values for keratin, oil, sensitivity, the number of hairs per hair follicle, hair thickness, erythema, and pustules in a form of score using a plurality of scalp photographed image data and labeling data.

The learning unit may perform tokenization pre-processing on the collected expert diagnosis script data using a tokenizer, and cause the second learning model to learn to generate the diagnosis script using the pre-processed expert diagnostic script data and labeling data.

The classification unit may acquire a result value for keratin among the measurement items according to the presence or absence of foreign substances in a scalp area, acquire a result value for oil among the measurement items according to the presence or absence of oil or foreign substances in an area corresponding to the hair, and acquire a result value for the sensitivity among the measurement items by comparing a pixel value of the scalp area with a reference pixel value (pixel value corresponding to red color).

The classification unit may acquire a result value for the number of hairs grown in the hair follicles included in each area by applying image processing business logic to the area corresponding to the hair follicle, extract a plurality of pixels having a value greater than a preset reference pixel value, count the extracted pixels to extract the number of pixels, and then use the number of extracted pixels and the calculated length value of one pixel to acquire the result value for the hair thickness.

The classification unit may acquire each result value for keratin, oil, sensitivity, erythema, and pustules from the first learning model, calculate an average value for the acquired each result value or extract the highest score among respective result values to classify a severity of the corresponding measurement item as high, medium, and low, and classify the scalp condition into at least one of dry, oily, sensitive, dandruff, atopic, seborrheic, complex, inflammatory, pustular, and folliculitis using classified severity.

The classification unit may set reference values for the number of hairs per hair follicle and the hair thickness, and compare and analyze the result value acquired from the first learning model and the reference value to classify the hair loss condition as at least one of normal, suspected hair loss, and progressing hair loss.

As described above, according to the present disclosure, it is possible to acquire expert analysis information on the scalp condition using the artificial intelligence algorithm, and to analyze the scalp condition and the hair loss condition.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 5 is an exemplary diagram showing reference items for scalp type classification in step S260 shown in FIG. 2; and FIG. 6 is an exemplary diagram showing reference items for diagnosing hair loss in step S260 shown in FIG. 2.

DETAILED DESCRIPTION OF THE PREFERRED EMBODIMENTS

Figure 1:
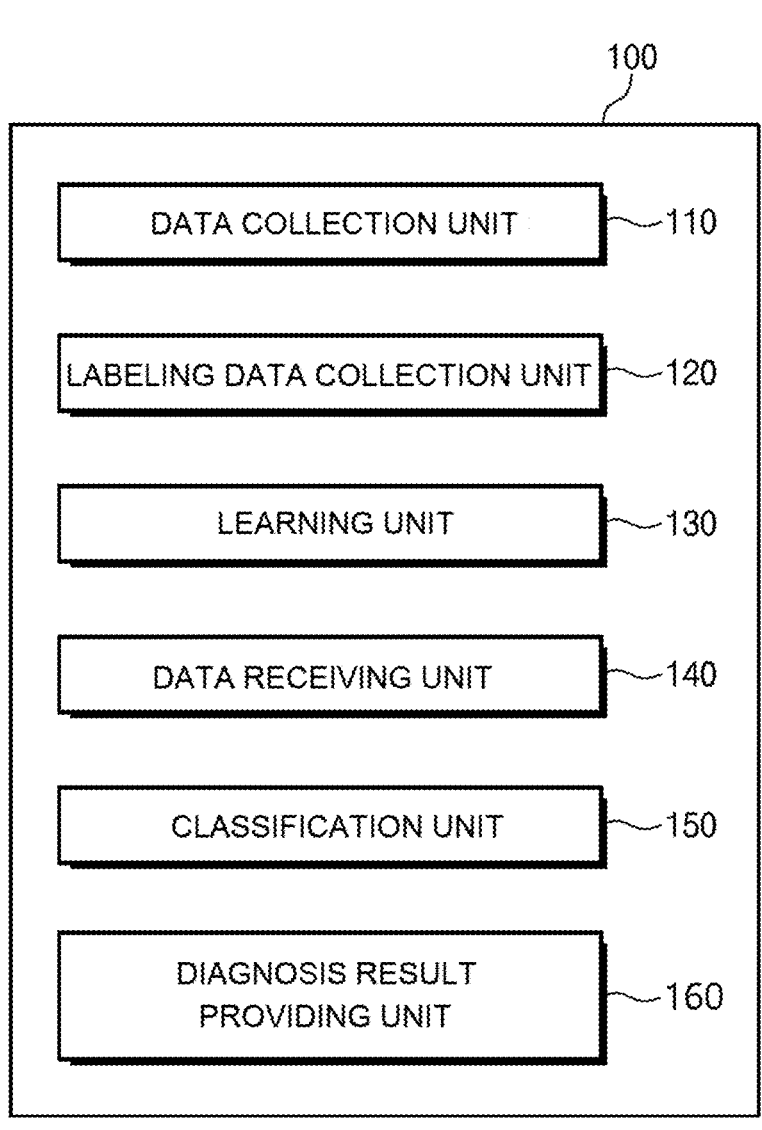
FIG. 1 is a configuration diagram for explaining a diagnostic script providing system according to an embodiment of the present disclosure.

Hereinafter, preferred embodiments according to the present disclosure will be described in detail with reference to the accompanying drawings. In this process, the thickness of lines or the size of components shown in the drawings may be exaggerated for clarity and convenience of explanation.

In addition, terms to be described later are terms defined in consideration of functions in the present disclosure, which may vary according to the intention or custom of a user or operator. Therefore, definitions of these terms will have to be made based on the content throughout this specification.

Hereinafter, a diagnostic script providing system for scalp and hair loss conditions according to an embodiment of the present disclosure will be described in more detail with reference to FIG. 1.

FIG. 1 is a configuration diagram showing the diagnostic script providing system according to the embodiment of the present disclosure.

As shown in FIG. 1, a diagnostic script providing system 100 according to the embodiment of the present disclosure includes a data collection unit 110, a labeling data collection unit 120, a learning unit 130, a data receiving unit 140, a classification unit 150, and a diagnosis result providing unit 160.

First, the data collection unit 110 collects scalp photographed image data and expert diagnosis script data.

The data collection unit 110 collects a plurality of scalp photographed image data from an operator or a server of a hospital performing hair loss treatment. Further, the data collection unit 110 collects expert diagnosis scripts matched with all or part of the plurality of scalp photographed image data.

The labeling data collection unit 120 collects labeling data received from the user. Here, the labeling data includes scores and keywords for each measurement item corresponding to the scalp photographed image data and the expert diagnosis script data. Here, the keyword may be extracted from the expert diagnosis script data.

The learning unit 130 builds a first learning model and a second learning model. Then, the learning unit 130 generates a first learning dataset using the scalp photographed image data and labeling data, inputs the generated first learning dataset into the first learning model, and causes the first learning model to learn to output scores for each measurement item.

In addition, the learning unit 130 generates a second learning dataset using the diagnostic script data and the labeling data, inputs the generated second learning dataset into the second learning model, and causes the second learning model to learn to output the diagnostic script.

Here, the first learning model and the second learning model are shown separately according to their functions, and each learning model may consist of a plurality of learning models.

In a state in which learning is completed, the data receiving unit 140 receives the scalp photographed image data of the patient to be diagnosed with a scalp condition and hair loss.

The classification unit 150 inputs the received scalp photographed image data into the first learning model to acquire the score for each measurement item, and uses the acquired score for each measurement item to classify the scalp condition, the hair loss condition, and severity of the corresponding patient.

Finally, the diagnosis result providing unit 150 generates a diagnosis script by inputting the classified patient's scalp condition, the hair loss condition, and the severity into the second learning model.

The diagnostic script providing system described above with reference to FIG. 1 may be implemented by hardware having a processor capable of processing and analyzing image data and script data.

Hereinafter, a method for providing a diagnostic script for scalp and hair loss conditions using the diagnostic script providing system 100 according to an embodiment of the present disclosure will be described in detail with reference to FIGS. 2 to 6.

Figure 2:
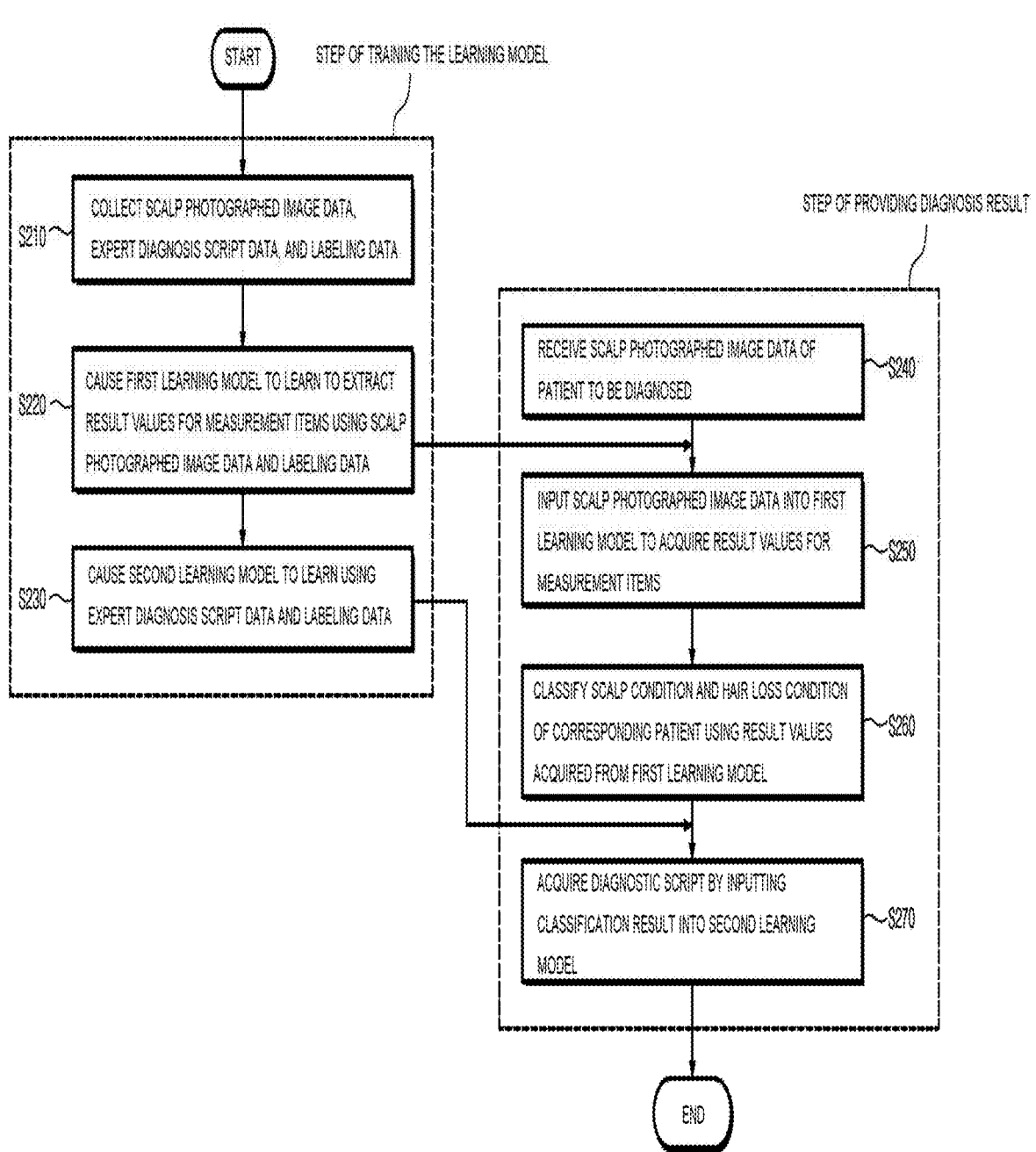
FIG. 2 is a flowchart for explaining a method for providing a diagnostic script for scalp and hair loss conditions using the diagnostic script providing system according to the embodiment of the present disclosure.

FIG. 2 is a flowchart showing the method for providing a diagnostic script for scalp and hair loss conditions using the diagnostic script providing system according to the embodiment of the present disclosure.

As shown in FIG. 2, the method for providing diagnosis results for scalp and hair loss conditions according to the embodiment of the present disclosure consists of a step of learning a plurality of learning models and a step of providing diagnosis results using the learning models.

First, the step of learning the plurality of learning models will be described. The diagnosis script providing system 100 collects the scalp photographed image data, the expert diagnosis script data, and the labeling data (S210).

In other words, the data collection unit 110 additionally collects the scalp photographed image data and the expert diagnosis script data corresponding thereto from a hospital server. In addition, the labeling data collection unit 120 collects the labeling data created by the user. Here, the labeling data includes scores and keywords for each measurement item, and the measurement item includes at least one of keratin, oil, sensitivity, hair thickness, the number of hairs per hair follicle, erythema, and pustules.

When step S210 is completed, the learning unit 130 causes the first learning model to learn to extract result values for measurement items using the scalp photographed image data and the labeling data (S220).

Figure 3:
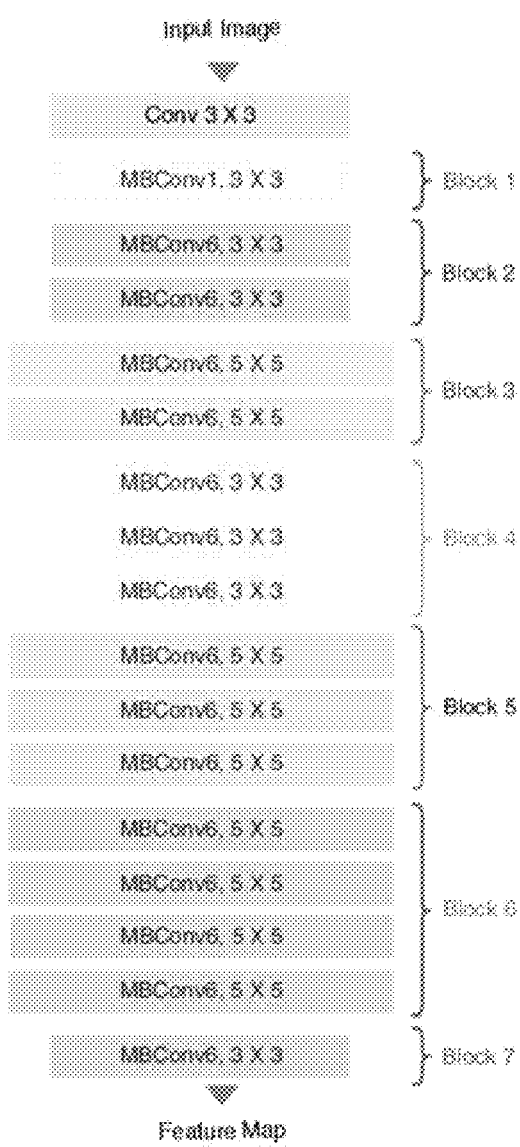
FIG. 3 is a diagram for explaining a first learning model to which an EfficientNet algorithm is applied according to an embodiment of the present disclosure.

FIG. 3 is a diagram for explaining the first learning model to which an EfficientNet algorithm is applied according to an embodiment of the present disclosure.

First, the learning unit 130 builds the first learning model to which the EfficientNet algorithm is applied. The first learning model is selected to efficiently adjust all the depth and width of the learning model and the size of the input image, and is configured of a total of 7 mobile inverted bottleneck convolution (MBConV) blocks as shown in FIG. 3. Instead of applying the convolution operation to all channels at once, the input scalp photographed image data is divided into each channel and the convolution operation is applied, so accuracy and speed may be improved.

The first learning model to which the above-described EfficientNet algorithm is applied may be used to extract result values for keratin, oil, and sensitivity among measurement items.

Figure 4:
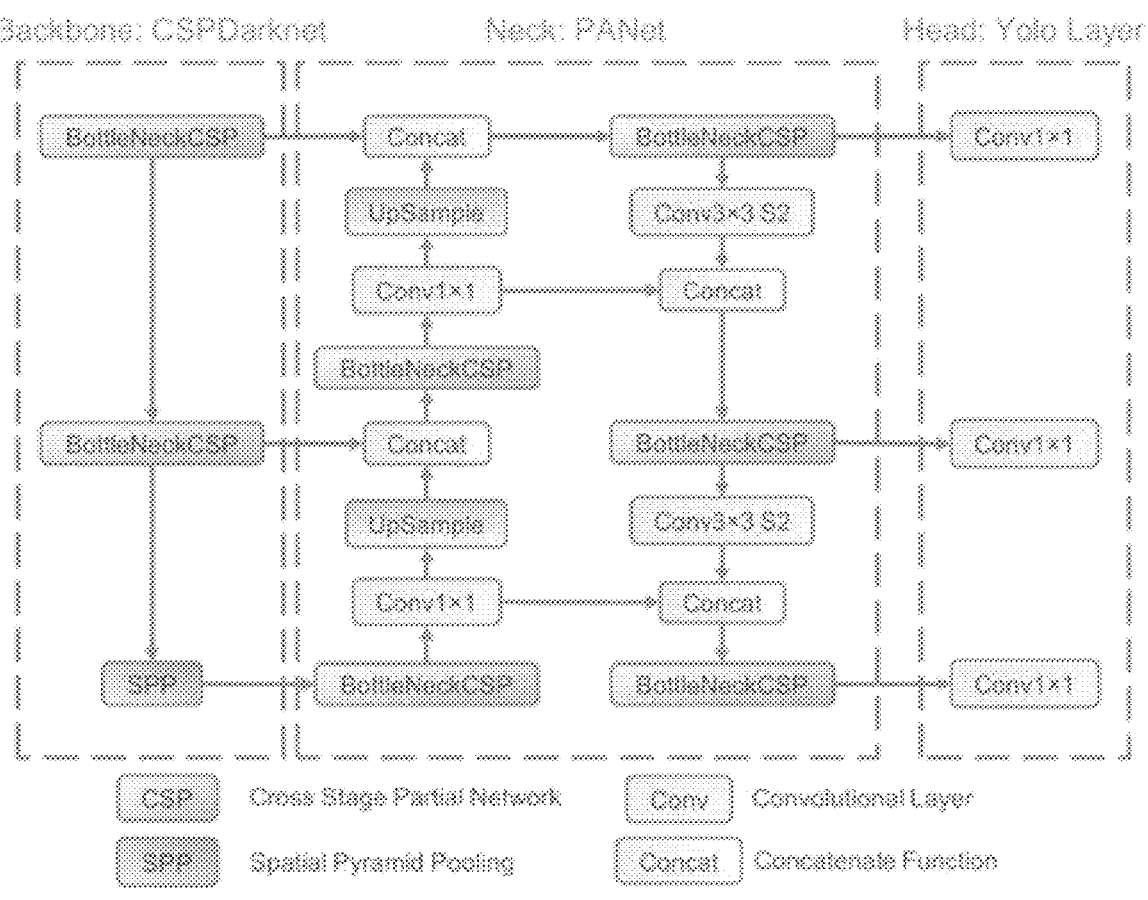
FIG. 4 is a diagram for explaining a first learning model to which a YOLOv5 detection algorithm is applied according to an embodiment of the present disclosure.

FIG. 4 is a diagram for explaining a first learning model to which a YOLOv5 detection algorithm is applied according to an embodiment of the present disclosure.

First, the learning unit 130 builds the first learning model to which the YOLOv5 detection algorithm is applied.

The first learning model to which the above-described YOLOv5 detection algorithm is applied may be used to extract result values for hair thickness, number of hairs per hair follicle, erythema, and pustules among measurement items.

Then, the learning unit 130 causes the first learning model to learn to extract result values for a plurality of measurement items using the scalp photographed image data and labeling data. As described above, the plurality of measurement items include keratin, oil, sensitivity, hair thickness, the number of hairs per hair follicle, erythema, and pustules.

When step S220 is completed, the learning unit 130 causes the second learning model to learn using the expert diagnosis script data and the labeling data (S230).

The learning unit 130 performs tokenization pre-processing on the collected expert diagnosis script data using a tokenizer.

In other words, the learning unit 130 tokenizes with the morpheme analyzer to cause the second learning model to learn. For example, assuming that the conventional diagnosis script data is "mildly oily scalp and the number of hairs per hair follicle is less than the standard, and initial hair loss is expected", the learning unit 130 tokenizes 'mildly', 'oily', 'scalp', 'the', 'number', 'of', 'hairs', 'per', 'hair', 'follicle', 'is', 'less', 'than', 'the', 'standard', 'initial', 'hair', 'loss', 'is', and 'expected' and causes the second learning model to learn.

Next, the learning unit 130 uses a Transformer model to infer words, sentences, etc. that will follow, and learns the diagnostic script to be generated. For example, 'mild, severe, serious, dangerous, etc.' is inferred to oily, dry, sensitivity, etc.'. In addition, as words following 'scalp, hair, etc.', 'is, as, etc.' is inferred. As words following 'hair thickness, number of hairs per hair follicle, etc. 'is, etc.' is inferred. In addition, as words following 'normal, less than standard, etc.', 'is, as, etc.' is inferred, and words following 'initial hair loss, hair loss, normal, etc.' is 'is, as, etc, may be, expected' is inferred.

Accordingly, the learning unit 130 combines the inferred words and causes the second learning model to learn to generate a diagnosis script, for example, 'it is mildly oily scalp and the number of hairs per hair follicle is less than the standard, and hair loss is expected'.

When steps S210 to S230 are completed, the diagnostic script providing system 100 receives the scalp photographed image data of a patient to be diagnosed with a scalp condition and whether of hair loss (S240).

The data receiving unit 140 receives the scalp photographed image data obtained by photographing the patient's scalp. At this time, the patient transmits an image obtained by photographing the scalp while being connected to the diagnosis result providing system 100 through a terminal owned by the patient as a patient who has never received a scalp-related diagnosis. At this time, the examiner acquires a plurality of scalp photographed image data by photographing the patient's scalp from various angles.

Then, the classification unit 150 inputs the received scalp photographed image data into the first learning model to acquire result values for measurement items (S250).

In other words, the classification unit 150 inputs the scalp photographed image data into the first learning model. Then, the first learning model outputs result values for keratin, oil, sensitivity, the number of hairs per hair follicle, hair thickness, erythema, and pustules in the form of score from the input scalp photographed image data.

To explain this again, the first learning model analyzes the input scalp photographed image data and extracts a result value for keratin from measurement items according to the presence or absence of foreign substances in the scalp area.

In addition, the first learning model analyzes the input scalp photographed image data and extracts a result value for oil content among measurement items according to the presence or absence of oil or foreign substances in the area corresponding to the hair.

In addition, the first learning model analyzes the input scalp photographed image data and compares a pixel value of the scalp area with a reference pixel value (pixel value corresponding to a red color) to extract a result value for sensitivity among the measurement items.

In addition, the first learning model detects an area corresponding to the hair follicle from the input scalp photographed image data, applies image processing business logic to the detected area, and extracts the number of hairs grown in the hair follicles included in each area as the result value.

In addition, the first learning model extracts a plurality of pixels having a value greater than a preset reference pixel value, counts the extracted pixels to extract the number of pixels, and then uses the number of extracted pixels and the calculated length value of one pixel to extract the result value for the hair thickness.

Here, the reference pixel value represents a pixel value to be determined as hair, and a length value for one pixel calculated using the ratio of the thickness of hair in the scalp photographed image data to the actual hair thickness is set as the reference pixel value.

In addition, the first learning model detects a region corresponding to the scalp from the input scalp photographed image data, compares the pixel value in the detected region with the reference pixel value, and extracts result values for erythema and pustules.

Next, the classification unit 150 classifies the scalp condition and the hair loss condition of the corresponding patient using the result values acquired from the first learning model (S260).

First, the classification unit 150 classifies the severity into high, medium, and low using the result values of a plurality of measurement items acquired for each of a plurality of scalp photographed images. In other words, the classification unit 150 calculates an average score from each result value for keratin, oil, sensitivity, the number of hairs per hair follicle, hair thickness, erythema, and pustules, or extracts the highest score to classify the severity for each measurement item as high, medium, and low. In this case, the severity may be classified according to a preset score range.

Then, the classification unit 150 classifies the scalp condition using the severity of keratin, oil, sensitivity, erythema, and pustules.

FIG. 5 is an exemplary diagram showing reference items for scalp type classification in step S260 shown in FIG. 2.

As shown in FIG. 5, the classification unit 150 receives the severity of keratin, oil, sensitivity, erythema, and pustules within a preset range, and classifies the severity as any one scalp type among dry, oily, sensitive, dandruff, atopic, seborrheic, complex, inflammatory, pustular, and folliculitis. Here, as shown in FIG. 5, if the severity level of the measurement item which is shaded is high, the classification unit 150 classifies the shaded measurement item into a corresponding state.

For example, if the severity of keratin is high and the severity of oil and sensitivity is medium or low, the classifying unit 150 classifies the patient's scalp condition as dry.

In addition, if the severity of keratin is low and the severity of oil and sensitivity is high, the classifying unit 150 classifies the patient's scalp condition as seborrheic.

Next, the classification unit 150 classifies the hair loss state using the number of hairs per hair follicle and hair thickness.

FIG. 6 is an exemplary diagram showing reference items for diagnosing hair loss in step S260 shown in FIG. 2.

As shown in FIG. 6, the classification unit 150 sets reference values for the number of hairs per hair follicle and the hair thickness, and as shown in FIG. 6, depending on whether the shaded portion is applicable, the corresponding patient is classified as one of normal, suspected hair loss, and progressing hair loss.

When step S260 is completed, the diagnosis result providing unit 160 acquires a diagnostic script by inputting the classification result acquired in step S260 into the second learning model (S270).

The diagnosis result providing unit 160 acquires diagnosis script data from the second learning model by inputting the classification result according to the scalp condition and hair loss diagnosis acquired in step S260 to the second learning model.

At this time, since the second learning model has been learned to output data having a certain sentence structure via step S230, the diagnostic script data is processed to have a certain sentence structure using the input result value and the corresponding keyword. For example, "the patient is considered to have early hair loss due to thinning hair on a slightly oily scalp" is processed into "mildly oily scalp, hair thickness is the standard or less, and early hair loss is expected" and output.

As described above, the scalp condition diagnosis system according to the present disclosure may acquire expert analysis information on the scalp condition using the artificial intelligence algorithm, and analyze the scalp condition and the hair loss condition.

Although the present disclosure has been described with reference to the embodiments shown in the drawings, this is only exemplary, and those skilled in the art will understand that various modifications and equivalent other embodiments are possible therefrom. Therefore, the true technical protection scope of the present disclosure should be determined by the technical spirit of the claims below.

What is claimed is:

1. A system for providing diagnostic script, comprising:
a data receiving unit configured to receive scalp photographed image data of a patient to be diagnosed with a scalp condition and a hair loss condition;
a classification unit configured to input the received scalp photographed image data of the patient into a first learning model to acquire result values for a plurality of measurement items and classify the scalp condition and the hair loss condition using the acquired result values;
a diagnosis result providing unit configured to input information on the classified scalp condition and hair loss condition into a second learning model and output diagnosis script data for the patient;
a data collection unit configured to collect a plurality of scalp photographed images and a plurality of expert diagnosis scripts;
a labeling data collection unit configured to collect labeling data including scores and keywords for each measurement item corresponding to the scalp photographed images and the expert diagnosis scripts; and
a learning unit configured to:
build the first learning model using the scalp photographed images and the labeling data;
build the second learning model using the expert diagnosis scripts and labeling data;
cause the first learning model to learn to output the result values of the plurality of measurement items; and
cause the second learning model to learn to generate a diagnostic script using a classification result which is output through the first learning model,
wherein, to acquire a hair thickness among the measurement items, the classification unit is configured to:
extract a plurality of first pixels having a value greater than a preset reference pixel value, wherein the reference pixel value represents a pixel value to be identified as a hair;
count the extracted first pixels to extract the number of the first pixels; and
acquire the hair thickness by using the number of the extracted first pixels and a length of the first pixel, wherein the length of the first pixel is calculated using a ratio of a hair thickness in the scalp photographed image to an actual hair thickness.

2. The system for providing diagnostic script according to claim 1, wherein the measurement items include at least one of keratin, oil, sensitivity, the hair thickness, the number of hairs per hair follicle, erythema, and pustules.

3. The system for providing diagnostic script according to claim 1, wherein the learning unit is configured to cause the first learning model to learn to extract result values for keratin, oil, sensitivity, the number of hairs per hair follicle, the hair thickness, erythema, and pustules in a form of score using the scalp photographed images and the labeling data.

4. The system for providing diagnostic script according to claim 1, wherein the learning unit is configured to perform a tokenization pre-processing on the collected expert diagnosis scripts using a tokenizer, and cause the second learning model to learn to generate the diagnosis script using pre-processed expert diagnostic scripts and labeling data.

5. The system for providing diagnostic script according to claim 1, wherein the classification unit is configured to:
acquire a result value for keratin among the measurement items according to presence or absence of foreign substances in a scalp area,
acquire a result value for oil among the measurement items according to presence or absence of oil or foreign substances in a hair area; and
acquire a result value for sensitivity among the measurement items by comparing pixel values of the scalp area with a reference pixel value which is a pixel value corresponding to red color.

6. The system for providing diagnostic script according to claim 1, wherein the classification unit is configured to acquire a result value for the number of hairs grown in each of hair follicles by applying image processing business logic to a hair follicle area.

7. The system for providing diagnostic script according to claim 1, wherein, the classification unit is configured to:

acquire result values for keratin, oil, sensitivity, erythema, and pustules from the first learning model, calculate an average value for the acquired the result values for each of the keratin, the oil, the sensitivity, the erythema, and the pustules or extract a highest score among the result values for each of the keratin, the oil, the sensitivity, the erythema, and the pustules to classify a severity for each of the keratin, the oil, the sensitivity, the erythema, and the pustules as high, medium, and low; and classify the scalp condition into at least one of dry, oily, sensitive, dandruff, atopic, seborrheic, complex, inflammatory, pustular, and folliculitis using the classified severity.

8. The system for providing diagnostic script according to claim 6, wherein the classification unit is configured to:

set reference values for the number of hairs per hair follicle and the hair thickness; and compare and analyze the result values acquired from the first learning model and the reference values to classify the hair loss condition as at least one of normal, suspected hair loss, and progressing hair loss.

\* \* \* \* \*